United States Patent [19]

Hoffmann et al.

[11] Patent Number: 5,000,177
[45] Date of Patent: Mar. 19, 1991

[54] BIPOLAR LEAD ADAPTER WITH RESILIENT HOUSING AND RIGID RETAINERS FOR PLUG SEALS

[75] Inventors: Colleen M. Hoffmann, Forest Lake; Donald L. Sandford, Lakeland; Susan M. Walgren, Shoreview; David W. Mayer, Bloomington, all of Minn.

[73] Assignee: Cardiac Pacemakers, Inc., St. Paul, Minn.

[21] Appl. No.: 471,604

[22] Filed: Jan. 29, 1990

[51] Int. Cl.⁵ ............................................. A61N 1/372
[52] U.S. Cl. .................................................. 128/419 P
[58] Field of Search ............................. 128/419 P, 784

[56] References Cited

U.S. PATENT DOCUMENTS

| | | | |
|---|---|---|---|
| 3,822,707 | 7/1974 | Adducci et al. | 128/419 P |
| 3,908,668 | 9/1975 | Bolduc | 128/419 P |
| 4,412,916 | 11/1983 | Keel | 210/90 |
| 4,461,194 | 7/1984 | Moore | 81/436 |
| 4,479,489 | 10/1984 | Tucci | 128/419 P |
| 4,583,543 | 4/1986 | Peers-Trevarton | 128/419 P |
| 4,774,953 | 10/1988 | Foote | 128/419 P |
| 4,784,141 | 11/1988 | Peers-Trevarton | 128/419 P |
| 4,932,409 | 6/1990 | Hirschberg | 128/419 P |

Primary Examiner—William E. Kamm
Assistant Examiner—Scott M. Getzow
Attorney, Agent, or Firm—Haugen and Nikolai

[57] ABSTRACT

An adapter for extending a sensing and stimulation delivery lead in a body stimulation system, such as a cardiac pacer or cardioverter defibrillator, includes a resilient, electrically insulative housing with a longitudinal barrel extended through the majority of the housing length for the insertion of a lead terminal connector. Two spaced apart transverse bores are formed in the housing, open to barrel and to the housing exterior. Two connector assemblies are mounted in the housing and positioned to receive respective pin and ring terminals of the lead when inserted into the barrel. Each connector assembly can be adjusted to secure the lead in the housing, by a tool inserted through one of the transverse bores. Each connector assembly is isolated from the housing exterior by a seal means mounted in the associated bore. Each seal means includes a seal member elastically deformable to admit a tool to the associated connector assembly via a passage through the seal member. A rigid retaining sleeve, secured within the associated bore, surrounds and slightly compresses its associated seal member to ensure that the passage remains closed when not admitting the tool.

19 Claims, 2 Drawing Sheets

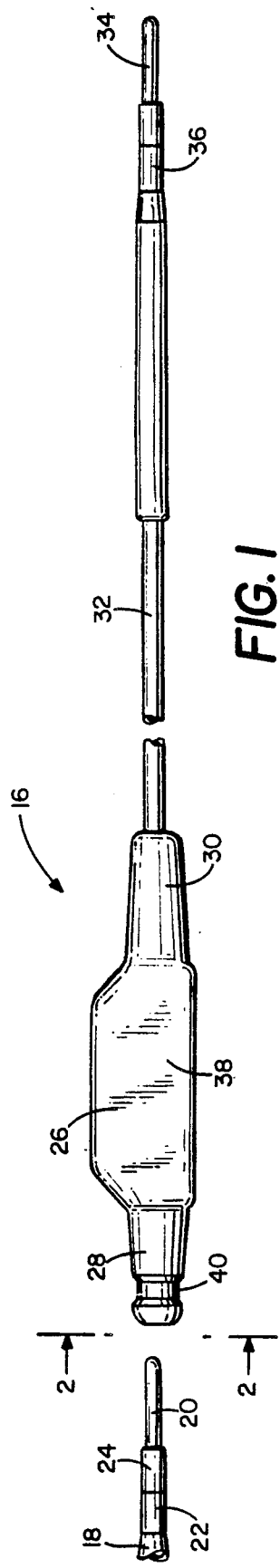
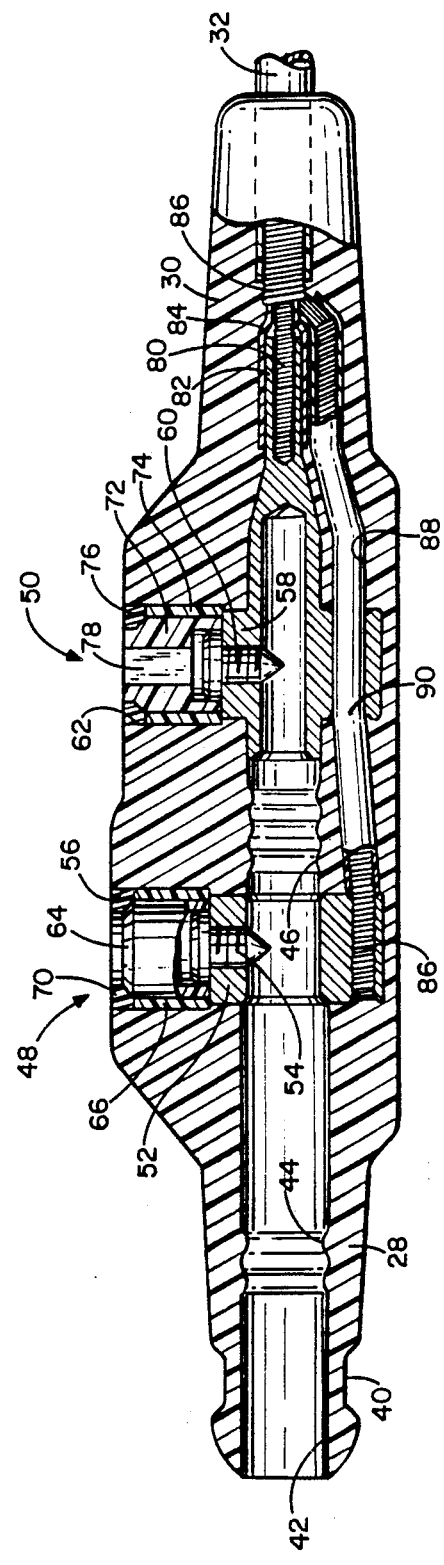

BIPOLAR LEAD ADAPTER WITH RESILIENT HOUSING AND RIGID RETAINERS FOR PLUG SEALS

BACKGROUND OF THE INVENTION

The present invention relates to body implantable connecting devices for extending cardiac pacing leads, defibrillation leads and the like, and more particularly to means for sealing electrically conductive connectors in such devices.

Certain particularly useful medical treatment systems involve body implantable devices that deliver pulses of electrical energy to stimulate body tissue. Perhaps the best known of these devices is the cardiac pacer, which includes a pulse generator having a power source and electrical circuitry for generating timed electrical pulses. The pulses are delivered through an electrically conductive lead having proximal end terminals connected to the pulse generator, and one or more distal end electrodes secured to myocardial tissue (for example) at a location remote from the pulse generator.

A more recent stimulating device is the defibrillator, designed to terminate arrhythmias such as ventricular fibrillation or tachycardia, by application of one or more properly timed electrical pulses to the heart. The defibrillator differs from the pacer in that the electrical pulses involved are of greater intensity, and delivered only in response to sensing arrhythmias. Other devices, e.g. neuromuscular stimulators, involve implantable means for delivering electrical impulses to stimulate tissue.

In all of these devices, there is a need for electrically and mechanically coupling the proximal ends of leads to the remainder of the tissue stimulating system, in a manner which is convenient, yet preserves mechanical integrity and provides a highly conductive path for electrical pulses and electrically isolates the conductive path from surrounding bodily tissue. Further, given the limited time and other constraints of implant procedures, it is desirable to provide connection means conveniently accessible to alternatively connect and disconnect the proximal end lead terminals. The connection can occur at a pulse generator, or at an adapter used between electrical leads of different sizes or types, or simply to extend the length of the conductive path.

An example of such connection in a pacer is disclosed in U.S. Pat. No. 3,822,707 (Adducci et al), in which proximal segments 19 and 20 of a lead are received respectively in sleeves 24 and 25 in the pulse generator. The segments are retained by Allen head set screws, with insulating rubber plugs inserted after the screws to electrically isolate them from the body cavity environment. In U.S. Pat. No. 3,908,668 (Bolduc) terminal pins of a lead are inserted into receptacles provided in a pulse generator, and retained by set screws 42. A rubber grommet 54 is placed over the set screws and is pierced through at a pair of protrusions, to admit a tool for turning the set screws. The grommet self seals when the tool is withdrawn.

Other means for connecting leads to body implantable devices are shown in U.S. Pat. No. 4,461,194 (Moore) in which a seal plug 36 is positioned between a set screw 32 and a cap 42, U.S. Pat. No. 4,583,543 (Peers-Trevarton) featuring an Allen screw with a pointed tip for forcing a side wall of a metal tube into contact with a lead terminal pin, and U.S. Pat. No. 4,784,141 (Peers-Trevarton) directed to a lead locking mechanism having a hollow screw coaxial with the lead being connected. In U.S. Pat. No. 4,774,953 (Foote), one end of a grub screw 32 protrudes into a lead retaining opening to secure the lead.

Plug seals having self-sealing passages have been found particularly advantageous in connection with cardiac pacers, as they afford quick and convenient tool access for securing lead terminal ends within a pulse generator, and for releasing such terminal ends. The capability of the plug to re-seal itself upon withdrawal of the tool, however, depends upon the dimensional integrity of the housing in which the plug is mounted. Pulse generators typically are constructed of rigid material well suited for this purpose, in that the diameter of openings containing the plugs is controlled. Adapters and lead extenders, however, frequently are constructed of silicone rubber or other resilient elastomeric material. Consequently the openings formed in such adapters for retaining plug seals do not provide the necessary rigidity, leading to alternative means for protecting the electrically conductive connectors housed in flexible adapters and the like.

For example, once the set screws have been adjusted to properly connect the lead, an uncured silicone rubber adhesive can be applied over the heads of the screws, to begin curing before the surgical site is closed. This adhesive, however, gives off acetic acid as it cures and can irritate the incision area. Once in place, this type of seal allows no further tool access. Another approach is to provide a flap seal which covers one or more opening containing set screws, and is sufficiently thin to be folded or rolled over upon itself to expose the openings and admit a tool to adjust the set screws. Flap seals are difficult to construct, however, and have a tendency to bond to themselves, which can result in a tearing of the flap as the physician attempts to move it into sealing position over the set screw openings.

Therefore, it is an object of the present invention to provide a reliable means for sealing terminal connection set screws in a flexible or resilient adapter, to electrically isolate the set screws and protect them from exposure to bodily fluids around the adapter.

Another object of the invention is to provide a means for sealing electrically conductive adjustable contacts, mounted within flexible housings, from the exterior of the housings and provide convenient access to adjust the contacts without removing the sealing means.

Yet another object of the invention is to provide a means for adapting selected plug mounting regions of a resilient adapter, such that the selected regions provide a controlled, rigid support of tool admitting and self-sealing plugs.

SUMMARY OF THE INVENTION

To achieve these and other objects, there is provided a body implantable device for forming an electrical and mechanical connection with an electrically insulative housing having a biocompatible exterior surface. A longitudinal bore is formed in the housing for receiving an electrically conductive terminal portion of an electrical lead. A second bore in said housing is open to the first bore and to the exterior surface. An electrically conductive connector means is mounted within the housing and positioned to receive the terminal portion when it is inserted into the longitudinal bore. The connector means is adjustable by a tool inserted into the second bore, to engage the terminal portion and thereby secure the lead in the housing. The connector means also is adjustable to release the lead. A biocompatible seal means provides electrical and fluid isolation of the connector means from bodily fluids proximate the exterior surface. The sealing means includes a resilient, electrically insulative seal member contained in the second bore between the connector means and exterior surface. The seal member has a passage therethrough and is elastically deformable to allow insertion of the tool into the second bore, through the passage and into an operable engagement with the connector means. Upon withdrawal of the tool, the seal member returns to a sealing configuration to close the passage and provide electrical and fluid isolation. The seal means further includes a rigid retaining means along a portion of a bore defining surface of the housing about the second bore. The retaining means is coaxial with the second bore, and surrounds and is contiguous with the seal member.

Typically the second bore is circular in cross-section. The preferred rigid retaining means is an annular sleeve having a radially outward surface contiguous with the bore defining surface and a radially inward surface contiguous with the seal member. The sleeve is preferably dielectric, with an exterior diameter slightly larger than the diameter of the second bore, and an interior diameter slightly less than the exterior diameter of the seal member. The interior diameter, in particular, is selected with care to frictionally support the plug seal, and promote the self-sealing of the seal member which accompanies tool withdrawal. The preferred seal member is a silicone rubber plug with a centrally located slit through the plug to form the passageway.

Alternatives to the preferred annular sleeve can be employed in providing the rigidity to support the seal plug. A curable coating, for example an epoxy resin, may be applied to the bore defining surface. The curing of the epoxy provides the rigidity required, with the cured coating finished or abraded if necessary to achieve the desired diameter. In cases where the adapter is constructed of a treatable material, selected regions of the adapter housing, in particular regions surrounding tool admitting bores, can be treated to increase their rigidity, leaving the remainder of the adapter resilient.

Another form of the invention resides in an improvement to a resilient adapter connected to a cardiac sensing and stimulation lead as a lead extension in a cardiac pulse generator system, such as a cardiac pacer or cardioverter defibrillator. The adapter includes a resilient, electrically insulative and biocompatible housing having a longitudinal bore therethrough, and first and second transverse bores open to the longitudinal bore and to the housing exterior. First and second electrically conductive connector assemblies are mounted in the housing to receive respective first and second terminal portions of a cardiac lead when the lead is inserted into the longitudinal bore. Each connector assembly includes a terminal receiving receptacle or socket, and a set screw adjustable by a tool inserted into a respective one of the first and second transverse bores.

The improvement comprises biocompatible first and second seal means which provide electrical fluid isolation of the connector assemblies from bodily fluid near the exterior surface. Each of the sealing means includes a resilient and electrically insulative seal member having a slit forming a passage through the seal member, elastically deformable to admit an insertion tool into the associated transverse bore, through the passage and into an operable engagement with the set screw. The seal member is self-sealing, closing the passageway upon tool withdrawal. Each seal mean further includes a rigid retaining means along a portion of a bore defining surface of the housing about is associated transverse bore The retaining means is coaxial with the second bore and in surrounding and contiguous relation to the associated seal member.

In accordance with the present invention, self-sealing plugs with tool admitting slits are conveniently employed in connection with adapters and other body implanted implements constructed of resilient materials, not only in cardioverter defibrillation systems but in connection with pacing, neuromuscular stimulation, bone growth stimulation and the like. The rigid retaining means may be retained within the tool access bores by friction, by a medical adhesive, or both. In any event, the retaining members surround and contain their associated plug seals, with their interior diameters selected to apply a predetermined radially inward compressive force upon the plugs to frictionally secure the plugs, and promote the plugs to self-seal when no tool is inserted through the passage. The sealing for adjusting connector set screws at any time deemed necessary or appropriate by the physician. Accordingly, the connection of an adapter or pulse generator with proximal end terminals of a lead can be quickly and conveniently accomplished, without unduly distracting the physician's attention from the surgical procedure at hand.

IN THE DRAWINGS

For a further appreciation of the above and other features and advantages, reference is made to the following detailed description and accompanying drawings in which:

FIG. 1 is a side elevation of a cardiac lead adapter constructed in accordance with the present invention;

FIG. 3 is a sectional view of the adapter, taken along the line 3—3 of FIG. 2;

Figure 5:
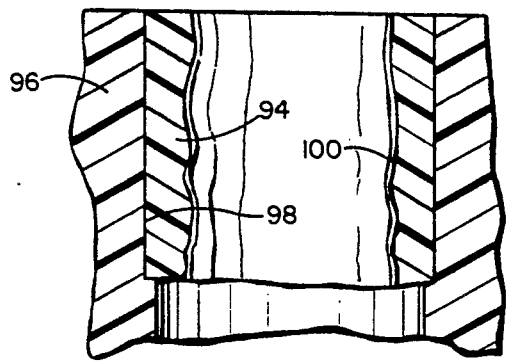
Figure 6:
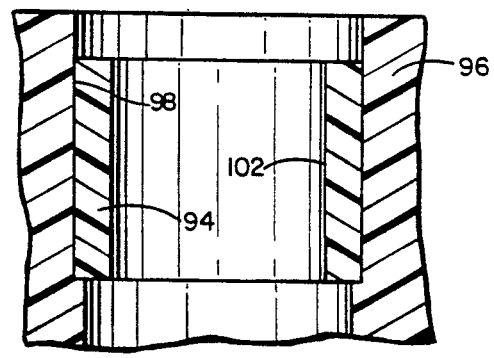
Figure 7:
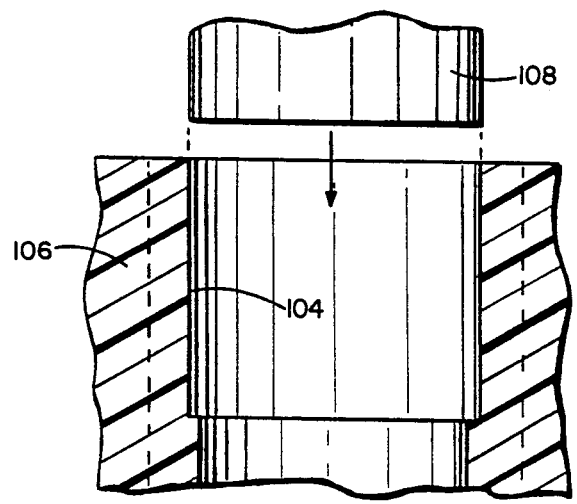

FIGS. 5 and 6 schematically illustrate an alternative embodiment plug seal retaining structure for the adapter; and FIG. 7 schematically illustrates yet another alternative embodiment plug seal retaining structure.

DETAILED DESCRIPTION OF THE PREFERRED EMBODIMENT

Turning now to the drawings, there is shown is FIG. 1 an adapter 16 suitable for electrical and mechanical coupling to the proximal end of a cardiac sensing and stimulation lead 18 in a cardiac pulse generation system. Lead 18 is bipolar and has two proximal end terminals, a pin terminal 20 and ring terminal 22. Terminals 20 and 22 are parts of separate electrically conductive paths contained within a dielectric sheath 24 of the lead. At the distal end of the lead (not shown) are bipolar electrodes, secured at or into myocardial tissue in a known manner, for the detection of intrinsic electrical activity (or its absence) and the delivery of stimulation pulses to the heart.

Adapter 16 provides a means for extending the length of the electrical path between the heart and a source of stimulation pulses. More particularly, the adapter includes an adapter housing or body 26 having a distal portion 28 adapted to receive the proximal end of lead 18 for releasable insertion. The housing preferably is a unitary molded member, formed of a soft and flexible material such as silicone rubber A proximal portion 30 of the housing provides strain relief about the distal end of a bipolar extender lead 32 permanently mounted to housing 26. At the proximal end of extender lead 32 are a pin terminal 34 and ring terminal 36 releasably connected to a pulse generator or other device (not shown) providing defibrillation pulses. An enlarged medial portion 38 of the housing contains a pair of connector assemblies, one associated with each of terminals 34 and 36. Each connector assembly releasably engages its associated one of terminal 20 and 22 for a mechanical mounting of defibrillation lead 18 within the housing. Each of the connector assemblies thus electrically couples it associated defibrillation lead terminal to an associated one of extender lead terminals 34 and 36. A groove 40 is formed about the circumference of distal portion 28 of the adapter housing, for locating an auxiliary ligature. When sutured at this location, the lead terminal is further stabilized within the adapter connector, and both articles may then be suture-anchored from groove 40 to subcutaneous tissue.

As seen from FIG. 3, a longitudinally extended barrel 42 is formed over the majority of the adapter housing length and is open to the housing distal end for receiving the proximal end of defibrillator lead 18. Radial reliefs are formed in the barrel, for example at 44 and 46, which compress sheath 24 to form a fluid seal and assist in retaining the lead within housing 26. Distal and proximal connector assemblies, mounted in the housing at 48 and 50 respectively, ensure a firm retention of lead 18 within the housing, and respectively establish an electrical coupling to ring terminal 22 and pin terminal 20 when the defibrillator lead is fully inserted into the housing.

Distal connector assembly 48 includes a distal receptacle 52 having a longitudinal socket coaxial with barrel 42, and a transverse set screw 54 threadedly engaged with a top portion of the receptacle. Set screw 54 can be turned to advance its tip downwardly into the socket or to react the tip from the socket. Set screw 54 preferably has an Allen head and is rotated by a hexagonal wrench (not shown) insertable into a transverse tool access bore 56 in housing 26, open to barrel 42 and to the exterior of the housing.

Proximal connector assembly 50 is somewhat similar to the distal connector assembly, and includes an electrically conductive receptacle 58 fixedly mounted in housing 26 and having a longitudinal socket coaxial with the barrel. A set screw 60 is threadedly engaged with receptacle 58, and can be advanced and retracted with the tool inserted into a tool access bore 62 in the same manner as set screw 54.

Figure 2:
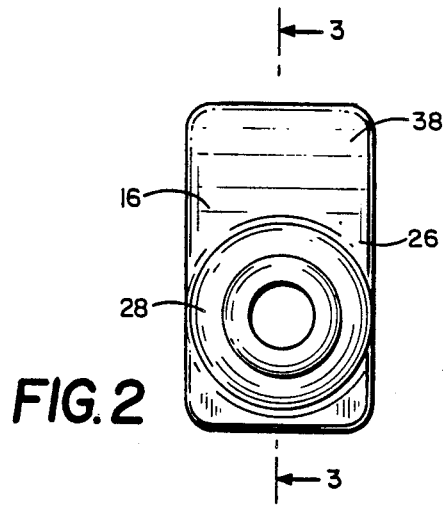
FIG. 2 is a front view of the adapter.
Figure 4:
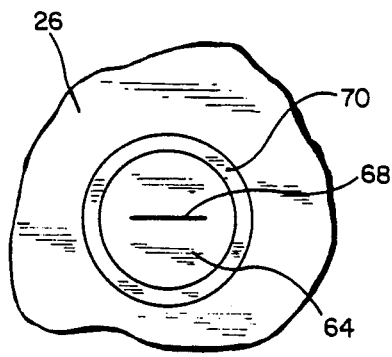
FIG. 4 is a top plan view of a portion of the adapter.

It is desirable to provide a fluid tight seal between the connector assemblies and the exterior of housing 26, as well as to electrically isolate the connector assemblies from bodily fluids and tissue. Distal and proximal seal assemblies are provided for this purpose, and are similar to one another in construction. The distal seal assembly, shown in FIGS. 3 and 4, includes a generally cylindrical plug seal 64 contained in bore 56 between connector assembly 48 and the housing exterior, and an annular retaining sleeve 66 surrounding the plug seal, concentric with and contained in bore 56. Plug seal 64, like the adapter housing, is flexible and preferably constructed of silicone rubber. Retaining sleeve 66 is a rigid member constructed of a polymer such as polysulfone, or a more rigid silicone rubber. As indicated at 68, a vertical passage is formed through the plug seal. When plug seal 64 is contained within retaining sleeve 66 as shown, passage 68 is closed, so that the plug seal provides both fluid and electrical isolation of connector assembly 48 from the environment about housing 26. However, plug seal 64 is deformable in the region about passage 68 to admit the tool from above, through the plug seal and into an operative engagement with set screw 54. Plug seal 64 and retaining ring 66 are bonded into bore 56 with a medical adhesive as indicated at 70. To ensure electrical isolation of connector assembly 48, the plug seal and retaining sleeve should be electrically insulative.

The proximal seal assembly is essentially similar to the distal sealing assembly, and includes a resilient plug seal 72 and a rigid annular retaining sleeve 74 surrounding the plug seal, retained in tool access bore 62 by a medical adhesive 76. A passage 78 admits a tool through the plug seal.

As previously mentioned, cardiac lead 18 and extender lead 32 are bipolar leads with two electrically conductive paths, electrically isolated from one another. Portions of extender lead 32 are shown in FIG. 3, to reveal that each conductive path is a helically wound metal coil. An inner coil 80 is received within a crimp tube 82 at the proximal end of the housing. The crimp tube is an extension of and thus electrically coupled to proximal receptacle 68 and also is contained within housing 26. An inner dielectric sheath 84 surrounds coil 80 and electrically isolates it from an outer coil 86. The outer coil is received into the housing along an opening 88 below crimp tube 82 and extending to distal receptacle 52, to electrically couple the outer coil and distal receptacle. A dielectric sheath 90 surrounds the outer coil. Each of coils 80 and 86 is permanently coupled with respect to its associated connector socket.

Salient features of the present invention include the rigidity of retaining sleeves 66 and 74, and the interior diameter of these sleeves in relation to the exterior diameter of their associated plug seals. In one particularly preferred approach, the retaining sleeves have an interior diameter of 0.150 inches, and are used with plug seals having exterior diameters of 0.159 inches. This provides an interference fit of each plug seal within its associated retaining sleeve, with a slight compression of the plug seal. The differences in plug seal and retaining sleeve diameters, in this case 0.009 inches, is selected to provide a predetermined amount of compression in the plug seals when retained in their associated sleeves. The predetermined comppredetermined compression ensures that the passage through the plug seal remains closed, except when the adjustment tool is inserted into and contained within the passage. A slight compression of each plug seal also enhances the contiguous engagement of its exterior surface and the interior surface of the associated sleeve, tending to frictionally secure the plug seal within the sleeve and improving the fluid seal.

The outer diameter of each sleeve is not so critical as its inside diameter, yet must be selected to ensure a fluid seal between the sleeve and housing 26 about the associated tool access bore, as well as to enhance frictional engagement. To these ends, the outside diameter of sleeves 66 and 74 is 0.18 inches, equal to the 0.18 inch diameter of tool access bores 56 and 62.

FIGS. 5 and 6 illustrate an alternative plug seal in the form of a coating 94 applied over a selected annular surface area of an adapter housing 96, in particular over a wall 98 of a tool admitting bore. Coating 94 is formed of a resin which is malleable when applied, but cures to become rigid. A surface 100 of the coating is abraded or otherwise finished to provide an annular radially inward surface 102 with a diameter corresponding to the predetermined amount of compression of a plug seal when contained in the tool admitting bore.

FIG. 7 illustrates yet another alternative approach in which a tool admitting bore 104 is formed in an adapter housing 106 formed of a material which is normally resilient, but treatable to become rigid, for example through heating to a predetermined temperature for a predetermined amount of time. A cylindrical tool 108, heated by an electrical element (not shown), is insertable into bore 104 to heat housing 106 in the region about the tool admitting bore. Following heating of this region, the tool is withdrawn and the region, once it cools, provides a rigid retaining structure for a plug seal.

Adapter 16 is connected to lead 18 first by inserting the proximal end of the lead into barrel 42 until pin terminal 34 is aligned with proximal connector assembly 50, and ring terminal 36 is aligned with distal connector assembly 48. Next, the hexagonal shaft of the tool is inserted through one of the plug seals, e.g. distal plug seal 64, and manipulated to tighten set screw 54 against ring terminal 22, whereupon the tool is withdrawn. The tool is similarly inserted through plug seal 72 to tighten set screw 60 against pin terminal 20. This secures lead 18 mechanically within housing 26, as well as establishing the electrical connections between ring terminals 22 and 36, and pin terminals 20 and 34. Finally, a ligature is secured around housing 26 at groove 40, to further mechanically secure lead 18 with respect to housing distal portion 28.

Should the need arise to adjust the positioning of lead 18 within housing 26, or to remove adapter 16 for inspection or for replacement, release of lead 18 is conveniently accomplished by reinsertion of the tool through plug seals 64 and 72 to retract the respective set screws. Plug seals 64 and 72 readily yield to accept the tool through passages 68 and 78, respectively. The flexible adapter housing can yield as well, if necessary, particularly in regions near tool access bores 56 and 62. This accommodates the alignment of the tool coaxially with each set screw, and reduces the risk of damage to the associated plug seal passage in the event that the passage is not coaxial with the set screw. Thus, tolerances for plug seal and passage alignment are less strict, and demands upon the physician's attention are less severe, permitting the physician to concentrate more fully upon the surgical procedure underway.

What is claimed is:

1. A body insertable device forming an electrical and mechanical connection with an electrical lead, including:
    a resilient and electrically insulative housing having a biocompatible exterior surface;
    a longitudinal first bore in said housing for receiving an electrically conductive terminal portion of an electrical lead, and a second bore in said housing open to the first bore and to the exterior surface;
    an electrically conductive connector means mounted within said housing and positioned to receive the terminal portion when said lead is inserted into said first bore, said connector means being adjustable, by a tool inserted into said second bore, to engage said terminal portion and thereby secure said lead in the housing, and alternatively release said lead; and
    a biocompatible sealing means for providing electrical and fluid isolation of said connector means from bodily fluids proximate said exterior surface, said sealing means including a resilient and electrically insulative seal member contained in said second bore between said connector means and said exterior surface, said seal member having a passage therethrough and being elastically deformable to allow insertion of said tool into the second bore through the passage and into an operable engagement with the connector means, said seal member returning to a sealing configuration to close said passage and provide said isolation upon a withdrawal of said tool, said sealing means further including a rigid retaining means along a portion of a bore defining surface of said housing defining said second bore, said retaining means being coaxial with said second bore and in surrounding and contiguous relation to said seal member.

2. The device of claim 1 wherein:
said second bore is circular and said rigid retaining means comprises an annular sleeve having a radially outward surface contiguous with said bore defining surface, and a radially inward surface contiguous with said seal member.

3. The device of claim 2 wherein:
said annular sleeve is electrically insulative.

4. The device of claim 2 wherein:
the exterior diameter of said annular sleeve is at least as large as the diameter of said second bore, and the interior diameter of said sleeve is slightly less than the exterior diameter of said seal member.

5. The device of claim 2 wherein:
said seal member comprises a plug constructed of silicone rubber, and said passageway comprises a slit through said plug.

6. The device of claim 1 wherein:
said rigid retaining means comprises curable coating applied to said bore defining surface and hardening upon curing.

7. The device of claim 1 wherein:
said rigid retaining means comprises a selected region surrounding and including said bore defining surface and treated to become rigid.

8. The device of claim 1 wherein:
said second bore is transversely oriented.

9. The device of claim 1 wherein:
said connector means comprises a receptacle having a socket opening coaxial with said first bore and an aperture coaxial with said second bore, and a fastener contained in said aperture and movable by said tool toward and way from said socket opening.

10. The device of claim 9 wherein:
said aperture is surrounded by internal threads, and said fastener comprises a screw having external threads conforming to the internal threads surrounding said aperture, and said tool comprises a driving tool for turning said screw.

11. The device of claim 1 further including:
at least one further bore in said housing open to the first bore and to the exterior surface;
a further electrically conductive connector means mounted within said housing and positioned to receive a further terminal portion of said lead when the lead is inserted into said first bore, said further connector means being adjustable, by said tool inserted into the further bore, to alternatively engage and release the further terminal portion; and a further biocompatible sealing means including a resilient and electrically insulative further seal member contained in said further bore between the further connector means and the exterior surface, and a further rigid retaining means surrounding and contiguous with the further seal member and disposed along a bore defining surface defining said further bore.

12. A resilient adapter forming an electrical and mechanical connection with a bipolar lead, including:

a resilient and electrically insulative adapter housing, with at least an exterior surface of said housing being biocompatible;

a longitudinal first bore in said adapter housing for receiving an electrically conductive terminal portion of a lead, and second and third bores in said housing, each open to said first bore and to said exterior surface;

electrically conductive first and second connector assemblies mounted within said housing and positioned to receive respective first and second terminals of said terminal portion when said lead is inserted into said first bore, each of said connector assemblies including a terminal receiving receptacle having a socket aligned with said longitudinal first bore, and a fastener mounted in said receptacle and adjustable by a tool inserted into its associated one of said second and third bores, to engage said terminal portion at its associated one of said first and second terminals and thereby secure said lead with respect to said adapter housing, said fasteners further being adjustable to release said lead; and first and second biocompatible sealing means for providing electrical and fluid isolation of said first and second connector assemblies, respectively, from bodily fluids proximate said exterior surface, each of said sealing means including a resilient and electrically insulative seal member contained in an associated one of said second and third bores between its associated connector assembly and said exterior surface, each seal member having a passage therethrough and being elastically deformable to allow insertion of said tool into its associated one of said second and third bores through the passage and into an operable engagement with the associated connector assembly, each seal member returning to a sealing configuration to close its associated passage and provide said isolation upon withdrawal of said tool, each sealing means further including a rigid retaining means along a bore defining surface of said housing defining its associated one of said second and third bores each said retaining means being coaxial with its associated bore and in surrounding and contiguous relation to its associated seal member.

13. The adapter of claim 12 wherein:

said second and third bores are circular and said rigid retaining means comprise first and second annular sleeves, each sleeve having a radially outward surface contiguous with its associated bore defining surface, and a radially inward surface contiguous with its associated seal member.

14. The adapter of claim 13 wherein:

said annular sleeves are electrically insulative.

15. The adapter of claim 14 wherein:

the exterior diameter of said annular sleeves is at least as large as the diameter of said second and third bores, and the interior diameter of said sleeves is slightly less than the exterior diameter of said seal members.

16. The adapter of claim 15 wherein:

said seal members comprise plugs constructed of silicone rubber, and said passageway in each plug comprises a slit through said plug.

17. The adapter of claim 12 wherein:

said second and third bores are transversely oriented.

18. The adapter of claim 12 wherein:

said first and second connector assemblies each comprise a receptacle having a socket coaxial with said first bore, an aperture coaxial with the associated one of said second and third bores, and a fastener contained in it associated one of said apertures and movable by said tool toward and away from the associated socket.

19. The adapter of claim 18 wherein:

said apertures are threaded, and said fasteners comprise screws having external threads conforming to the threads of said apertures, and said tool comprises a driving tool for turning said screws.

* * * * *